Oct. 23, 1934. M. H. HORVATH Plant Pat. 110
BARBERRY
Filed July 19, 1934
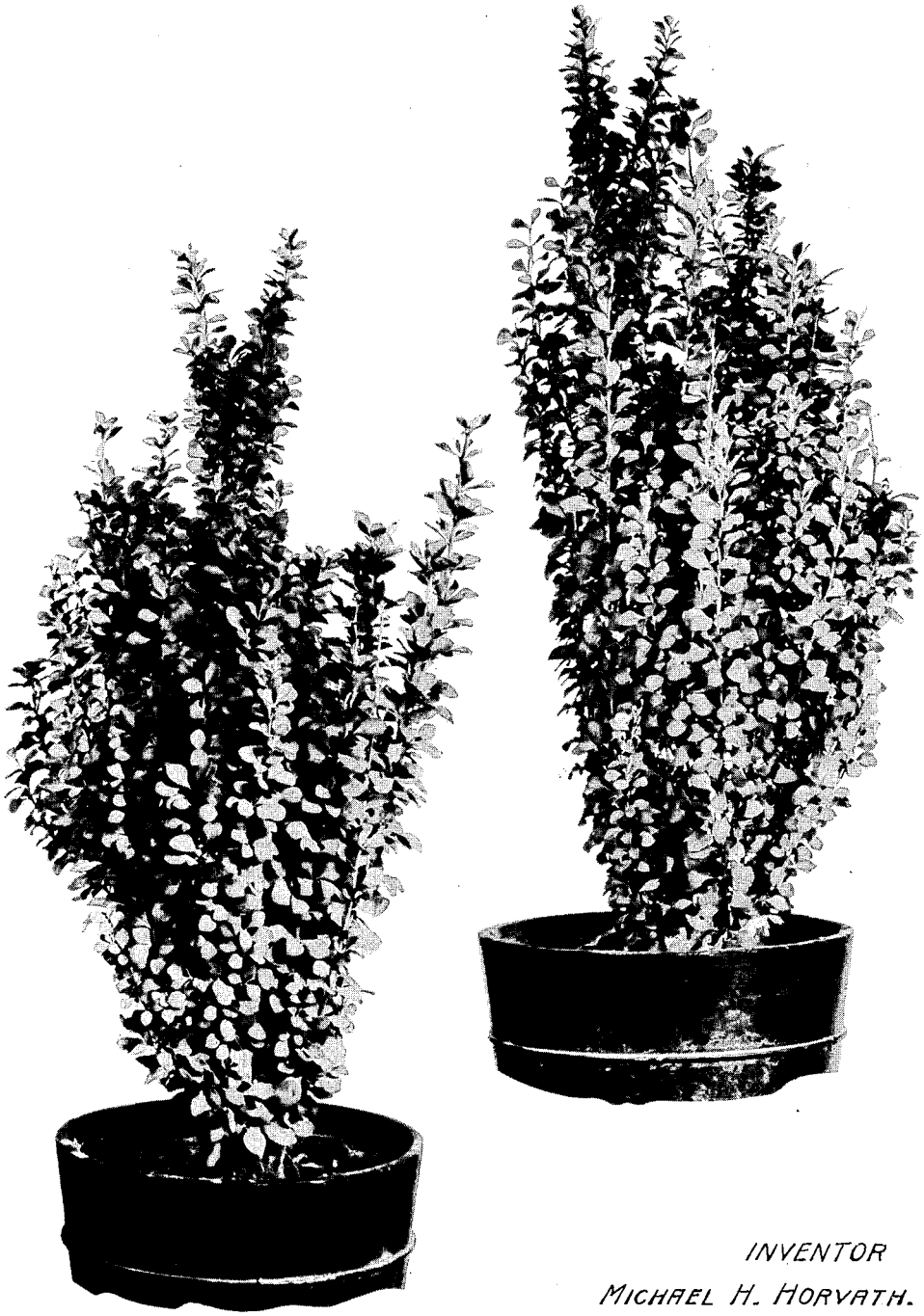
INVENTOR
MICHAEL H. HORVATH.
Robb & Robb
ATTORNEYS.

Patented Oct. 23, 1934

UNITED STATES PATENT OFFICE

110

BARBERRY

Michael H. Horvath, Mentor, Ohio, assignor to The Cole Nursery Company, Painesville, Ohio, a corporation Application July 19, 1934, Serial No. 736,123

1 Claim. (Cl. 47—59)

My new Berberis was produced in the fifth generation of seedlings from *Berberis thunbergi pluriflora*, the original parent plant having been a type with growth tending upright of *Berberis thunbergi pluriflora*. From each one of the five generations mentioned above the most upright plants were selected until the fifth generation in which I found the perfectly upright growing type of these Letters Patent.

It is well known that the common Japanese barberry used largely for hedges embodies an irregular plant or bush growth which gives a somewhat open and ragged appearance unless it is maintained neatly trimmed. Moreover, when the Japanese barberry hedge is cut or trimmed, the cutting away of the fresh or new growth and foliage, necessary to give regularity to the hedge, causes ugliness of the plants or bushes because of the exposing of the stalk temporarily and at least until new growth is formed.

One of the results achieved in the use of my new variety of Berberis lies in the fact that it grows in a pyramidal and upright manner so as to avoid the need of the periodical deep trimming of the ordinary Japanese barberry. In other words, my new barberry, instead of growing like the Japanese barberry with spreading horizontal and some nearly procumbent or slightly ascending branches and branchlets, has the habit of growth with its branches and branchlets ascending, or being perfectly erect. This affords for my new variety of plant a growing shape with the branches and branchlets ascending and being perfectly upright so that with comparatively little trimming, usually only of the tips of the branches, with possible slight trimming on the sides, such shape may be maintained, and it is not required incident to the trimming that the new growth or foliage be cut back to the extent of exposing stalk or branchlet structure of the plant or bush. Thickness or density of the foliage likewise prevents exposure of the stalk when trimming is done.

In addition to the foregoing advantages, my barberry presents the appearance of a deep green colored foliage as distinguished from the appearance of lighter green coloring of the ordinary or common Japanese barberry, and I shall later set forth the reason for such deeper green appearance. A very important feature is that my plant has the rust-immune character of *Berberis thunbergi* so that Government permits are not required for interstate movement of this variety under the government regulations of the black stem rust quarantine. So far as I am advised I am the first to develop an erect growing *Berberis thunbergi*.

The prominent distinctions and characters of my new variety of Berberis, which has been asexually reproduced, are pointed out and become fully apparent by reference to the following description and to the annexed drawing, in which the views illustrate the general erect and/or pyramidal shape of my new variety of plant, and the drooping leaf character as well.

*Description*

*Plant growth.*—The growth of the plant appears to be almost perfectly uniform in my new variety as distinguished from the common *Berberis thunbergi*, wherein the natural growth is usually very straggly except when the plant is heavily trimmed as when used in hedges. The foliage is extremely dense and much heavier than the common *Berberis thunbergi*, for which reason the value of this new plant is enhanced. The growth of the plant is likewise unique and advantageous for use as a specimen shrub plant where formal effects are desired. This is due to the fact of the uniformity with which the plant grows with erectness of the ascending branches and branchlets affording the comparative uniformity of shape previously mentioned. Thus, by slight trimming the plant can be brought into a very narrow spire or pyramid, even to the ratio of one-fourth to one-third as wide as its height, something which cannot be achieved in the use of the common Japanese barberry plants. My new variety of Berberis may also be very satisfactorily trimmed to formal box-shaped plants.

It is found that the branches and branchlets of my new barberry are much stiffer and stronger and somewhat larger in cross section than the branches of the Japanese barberry.

*Coloring.*—My new Berberis possesses a foliage in which the leaves have the appearance in the growing plant of a green which is much darker than that of common *Berberis thunbergi*. I say appearance because on comparing the leaves separated from the plant, with the *thunbergi* species, the color seems much the same. I account for the apparent increased depth of green color in my growing plants to the fact that the foliage is much more dense than in the Japanese barberry. Moreover, in the latter many leaves appear to grow with their under and lighter green sides outermost or visible from the sides of the plant, thus presenting to the eye such lighter color. In my plant the leaves grow not only closer together, but with a sort of droop or downcurve that presents their darker colored upper sides primarily to the viewer and thus creating the appearance of the deeper green shade above referred to. The fact that the leaves of my new plant are thicker than the prior variety mentioned doubtless additionally accounts for the said deeper green effect.

The fall coloring of the foliage of my new variety takes on very deep, rich, and colorful autumn hues essentially darker in their shading when compared with the common *Berberis thunbergi.* The berries stay on the plants for about the same length of time as in reference to the common barberry.

*Leaf formation.*—In addition to the distinction of the leaf coloring previously pointed out, my Berberis has leaves of much greater length than found in the common barberry. Whereas in respect to *Berberis thunbergi* under certain conditions the leaves grow approximately ⅝″ to $\frac{11}{16}$″ in length, in my new variety of Berberis under the same conditions the growth runs approximately ¾″ to 1¼″. A somewhat increased breadth of the leaf formation is also notable, for in my new plant this breadth runs some $\frac{3}{16}$″ to $\frac{9}{16}$″ as compared with the customary breadth of the common barberry leaf which runs ¼ to $\frac{7}{16}$″ all under same conditions as above. I have noticed also an increase in the average thickness of the leaf, which seems to approximate some .0010 of an inch thickness increase as compared with *Berberis thunbergi.*

*Blossoms and fruit.*—The blooming period of my new Berberis is slightly later than that of Japanese barberry. The ripe fruit is a brilliant red in color similar to that of *Berberis thunbergi.* The flowers of my new variety are inconspicuous and appear very similar to those of the variety *Berberis thunbergi.* Also the fruit appears to be somewhat more elongate than that of *Berberis thunbergi.* The flowers are borne in the axils of the leaves usually in multiples of 3 to 10 instead of 1 to 3 as is the case with *Berberis thunbergi.*

Undoubtedly the most striking features of my barberry, as hereinbefore described, lie in the decided erectness of the plant with the branches and branchlets growing in an approximately vertical ascending direction, and the appearance of greater depth of green color of the leaves, all of which tends to especial advantage in the employment of my barberry for hedge purposes. Especial economy may be obtained in respect to hedge growths by the elimination of a considerable portion of the periodical trimming customarily found necessary with *Berberis thunbergi.*

My new plant has been found to be especially hardy in growth in the Ohio territory, withstanding temperatures as low as twenty-six degrees below zero without any touch of winter injury, all tip buds as far as ascertainable remaining perfectly alive. As previously mentioned, my Berberis is rust-immune.

I have found by asexual reproduction that the characteristics of my new variety of barberry are permanent.

I have set forth herein the most notable features of my invention by a comparison thereof with those varieties of the same class which closely resemble the same. It is apparent that my new *Berberis thunbergi pluriflora* is endowed with individual identity and is characterized truly as a new and distinct variety, as manifested by the several unusual and new characters that have been hereinbefore set forth.

I wish it to be understood that the characteristics which I have pointed out in connection with my new barberry plant in the foregoing specification, are typical, but doubtless subject perhaps to slight variation such as may be caused by change of environment.

What I claim as new is:

A new and distinct variety of *Berberis thunbergi* characterized particularly by its erectness and shapeliness of growth in the absence of trimming, approximating pyramidal form, and the dense growth of its foliage, as herein shown and described.

MICHAEL H. HORVATH.